United States Patent
Feklistov

(10) Patent No.: US 7,986,463 B2
(45) Date of Patent: Jul. 26, 2011

(54) BEAM BLOCKING AND COMBINING OPTIC

(75) Inventor: Dmitri Feklistov, Grange (AU); Oksana Feklistova, legal representative, Grange (AU)

(73) Assignee: Ellex Medical Pty Ltd (AU)

( * ) Notice: Subject to any disclaimer, the term of this patent is extended or adjusted under 35 U.S.C. 154(b) by 0 days.

(21) Appl. No.: 12/519,935

(22) PCT Filed: Dec. 12, 2007

(86) PCT No.: PCT/AU2007/001913
§ 371 (c)(1),
(2), (4) Date: Dec. 2, 2009

(87) PCT Pub. No.: WO2008/074057
PCT Pub. Date: Jun. 26, 2008

(65) Prior Publication Data
US 2010/0128356 A1 May 27, 2010

(30) Foreign Application Priority Data
Dec. 19, 2006 (AU) ................................ 2006907073

(51) Int. Cl.
*G02B 27/14* (2006.01)
(52) U.S. Cl. .................................................... 359/637
(58) Field of Classification Search .................. 359/580, 359/583, 584, 585, 586, 588, 589, 590, 629, 359/630, 634, 637
See application file for complete search history.

(56) References Cited

U.S. PATENT DOCUMENTS

| | | | |
|---|---|---|---|
| 5,634,923 A | 6/1997 | Brenner et al. | |
| 5,708,530 A * | 1/1998 | Huang | 359/634 |
| 5,817,088 A * | 10/1998 | Sterling | 606/4 |
| 5,954,711 A | 9/1999 | Ozaki et al. | |
| 5,966,240 A | 10/1999 | Lange et al. | |
| 6,312,423 B1 * | 11/2001 | Ota et al. | 606/4 |
| 6,611,383 B1 | 8/2003 | Lee | |
| 7,209,669 B2 * | 4/2007 | Kang et al. | 398/195 |
| 7,433,129 B2 * | 10/2008 | Riedmann | 359/629 |
| RE40,743 E * | 6/2009 | Fuerter et al. | 359/732 |
| 7,570,430 B1 * | 8/2009 | Peng et al. | 359/631 |
| 2002/0165525 A1 | 11/2002 | Nakamura | |

FOREIGN PATENT DOCUMENTS

| | | |
|---|---|---|
| EP | 1086674 | 3/2001 |
| JP | 1-155315 | 6/1989 |
| JP | 4-164444 | 6/1992 |

OTHER PUBLICATIONS

International Preliminary Report on Patentability from corresponding PCT/AU2007/001913 application, mailed Nov. 18, 2008.
International Search Report from corresponding PCT/AU2007/001913 application, mailed Feb. 8, 2007.

* cited by examiner

*Primary Examiner* — Ricky Mack
*Assistant Examiner* — Tuyen Tra
(74) *Attorney, Agent, or Firm* — Alston & Bird LLP

(57) ABSTRACT

A beam blocking and combining optic comprising a wedged optically transparent substrate with a hard dielectric coating applied to a beam combining side of the substrate. The coating has a high reflectance at a laser wavelength and high transmittance at visible wavelengths. The single optical component can combine laser beams into a viewing path and act as a laser safety filter to protect the viewer from reflected laser radiation while providing good color balance and very low astigmatism in the viewing path and very low astigmatism in the reflected laser beam.

16 Claims, 2 Drawing Sheets

BEAM BLOCKING AND COMBINING OPTIC

This invention relates to an optical element useful for combining a laser beam into a viewing path. In particular the invention provides beam blocking and combining that can combine a laser beam into a viewing path with very low astigmatism and provide laser safety protection to the viewer. The invention finds particular application in ophthalmic laser devices.

BACKGROUND TO THE INVENTION

In medical laser applications it is often required to combine a laser aiming beam and a laser treatment beam into the viewing path of a microscope to allow a practitioner to view a target area while the area is being treated with the laser beam. It is preferable that the method of combining the laser beams into the viewing path does not degrade the viewing quality or distort the laser beams. An important safety aspect of this arrangement is that the viewer is protected from scattered or reflected treatment beam laser radiation from the target.

Various methods have been used to attempt to achieve these requirements such as that described in United States patent application number 2002/0165525, assigned to Nidek Co Ltd. In this case a mirror is used to direct the laser beams into the viewing path and a separate protection filter is used to protect the viewer from laser radiation. A limitation of this design is that the mirror size and placement must be arranged to avoid interference with the viewing path.

Another arrangement is described in U.S. Pat. No. 5,634,923, assigned to Carl Zeiss Stiftung. The arrangement uses a deflecting optic which has a wavelength selective coating applied to it. The coating is designed so that it will be largely reflective at the treatment laser wavelength(s) used but non-reflective at other wavelengths. This allows the deflecting optic to be placed across the viewing path and has the added advantage that much of the reflected laser radiation is also reflected away from the viewing path. However, a laser protection filter is still required to meet safety requirements and the viewing quality is degraded by the wavelength selective coating which alters the viewing colour balance.

Another arrangement is described in U.S. Pat. No. 5,954,711, assigned to Nidek Co Ltd. In the Nidek arrangement a dichroic mirror is designed to combine the laser beam(s) into the viewing path and perform the function of a laser protection filter. This design also uses a wavelength selective coating, but in addition the substrate material is chosen to absorb any reflected laser radiation which comes into the viewing path. In this way a separate laser protection filter is avoided, however the viewing quality is limited by the change in colour balance in the viewing path.

The problem of altered colour balance is addressed in U.S. Pat. No. 5,966,240, assigned to Coherent Inc. In the Coherent arrangement the wavelength selective coating on the combining optic is designed to give the viewer a more natural colour balance, however a separate laser protection filter is still required.

Each of these combining optic designs using wavelength selective coatings also suffer from astigmatism which lowers the laser beam quality and degrades the viewing quality. This is caused by stress induced curvature of the optic caused by the coating process which introduces astigmatism to the laser beam(s) and also due to the use of angled parallel glass plates as a substrate which introduces astigmatism into the viewing path.

To reduce the stress induced curvature caused by the coating process the coating thickness needs to be kept to a minimum and the substrate thickness increased to resist the stress; however the substrate thickness needs to be kept to a minimum to minimize the astigmatism in the viewing path. These conflicting requirements usually result in a compromise design with a level of astigmatism in the laser beams and the viewing path and a coating which is not completely reflective at the treatment laser wavelength, thereby requiring a separate laser protection filter to be used.

An attempt to correct this astigmatism is described in Japanese Patent number 4164444, assigned to Nidek Co Ltd. Nidek uses a dichroic mirror that is curved. The curvature limits the usable size of the reflective area and a separate laser protection filter is still required.

The problem of astigmatism in laser devices has been addressed in some applications by using a wedge-shaped beam splitter. One typical example is described in U.S. Pat. No. 6,611,383, assigned to LG Electronics Inc. These applications do not have a requirement for a laser safety filter to protect a viewer and do not require thick dielectric coatings.

OBJECT OF THE INVENTION

It is an object of the present invention to provide a beam blocking and combining optic that ameliorates one or more of the identified problems in the prior art.

DISCLOSURE OF THE INVENTION

In one form, although it need not be the only or indeed the broadest form, the invention resides in a beam blocking and combining optic comprising:
a wedged optically transparent substrate with a hard dielectric coating applied to a beam combining side of the substrate, the coating having a high reflectance at a laser wavelength and high transmittance at visible wavelengths.

The wedge shape is designed with a wedge angle chosen to minimise astigmatism when viewing through the substrate.

The substrate material is selected so that the thermal expansion coefficient of the substrate matches that of the dielectric coating, in order to minimise stress and as a result minimise curvature of the substrate, resulting in further reduction of laser beam astigmatism.

The optically transparent substrate is suitably made between 2 mm and 5 mm thick at the central beam axis in order to reduce the curvature of the substrate caused by residual stress induced by the application of the dielectric coating, thereby resulting in minimal laser beam astigmatism.

Suitably the substrate has an anti-reflection coating on an opposite side of the substrate to the hard dielectric coating. The anti-reflection coating is designed to minimise reflection over the visible wavelength range.

The beam blocking and combining optic combines a laser beam into a viewing path with very low astigmatism in the viewing path and in the reflected laser beam. The hard dielectric filter coating applied to the beam combining side of the substrate is designed to be highly reflective at the laser wavelength in order to direct the laser beam into the viewing path and also act as a laser safety filter to protect the viewer from reflected laser radiation. The coating is specifically designed to maintain good colour balance in the viewing path using multiple layers to form an interference filter with controlled transmission over the visible spectrum in order to visually compensate for the wavelength range which is reflectively blocked.

By these means a single optical component can combine laser beams into a viewing path and act as a laser safety filter to protect the viewer from reflected laser radiation while providing good colour balance and very low astigmatism in the viewing path and very low astigmatism in the reflected laser beam which is an improvement over prior art designs.

BRIEF DETAILS OF THE DRAWINGS

To assist in understanding the invention preferred embodiments will now be described with reference to the following figures in which.

DETAILED DESCRIPTION OF THE DRAWINGS

Figure 1:
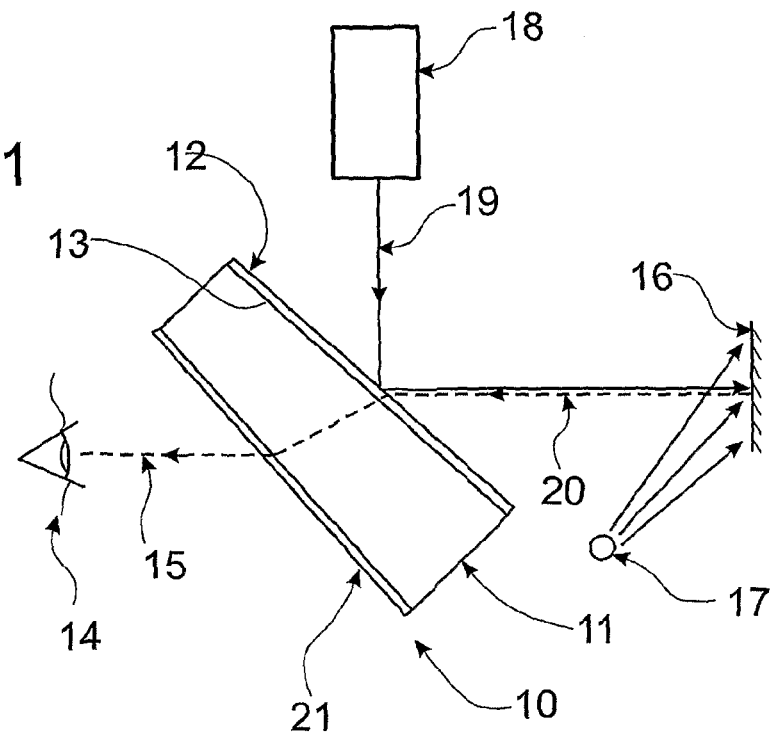
FIG. 1 is a block diagram showing the beam blocking and combining optic in a typical configuration.

In describing different embodiments of the present invention common reference numerals are used to describe like features.

Referring to FIG. 1, there is shown a beam blocking and combining optic 10 in a typical ophthalmic application. The optic 10 consists of a wedged substrate 11 with a hard dielectric coating 12 on a beam combining surface 13. The substrate 11 typically has a central thickness of 2 mm to 5 mm. A viewer 14 looks through the optic 10 along viewing path 15 to view target area 16. A white light source 17 is typically available to illuminate the target area 16.

A laser 18 is used to treat the target area 16. The hard dielectric coating 12 is designed to be highly reflective at the laser wavelength so that laser beam 19 from the laser 18 is reflected by the coating 12 into the target area 16. The coating 12 is specifically designed to maintain good colour balance in the viewing path 15 using multiple layers to form an interference filter with controlled transmission over the visible spectrum in order to visually compensate for the wavelength range which is reflectively blocked.

Laser radiation 20 is scattered from the target area back along the viewing direction but is blocked by the hard dielectric coating 12, thus protecting the viewer 14.

The substrate has an anti-reflection coating 21 on the opposite side of the substrate to the hard dielectric coating. The anti-reflection coating 21 is designed to minimise reflection over the visible wavelength range.

Figure 2:
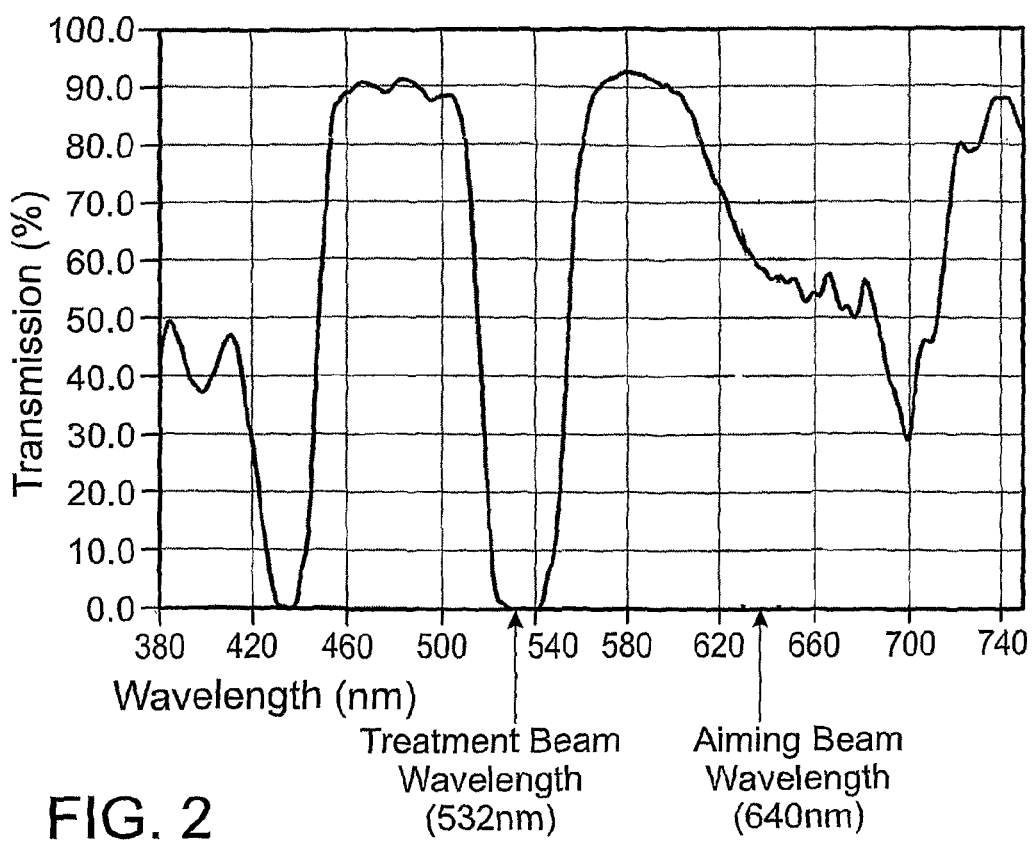
FIG. 2 is a graph showing a transmittance profile for one embodiment of a dielectric coating.

A typical transmission characteristic of the optic 10, which is produced by the correct colour balancing of coating 12, is shown in FIG. 2. In this example the laser treatment beam wavelength is 532 nm, in the green range, and transmission is minimized in a narrow range centered on this wavelength. To minimize the colour distortion caused by this rejection of green wavelengths, the transmission in the red region, above 580 nm is gradually reduced with increasing wavelength. Similarly, the transmission in the blue region, below 460 nm, is gradually reduced with decreasing wavelength. The result of this colour balancing is an essentially neutral colour, allowing a true colour image to the viewer 14.

FIG. 2 also shows an example of how a low power laser aiming beam may be used with optic 10. At the aiming beam wavelength the transmission is approximately 55% which allows a laser aiming beam, which is coaxial to the treatment beam 19, to be partially reflected onto the target 16 and partially transmitted along the viewing path 15 to the viewer 14.

Figure 3:
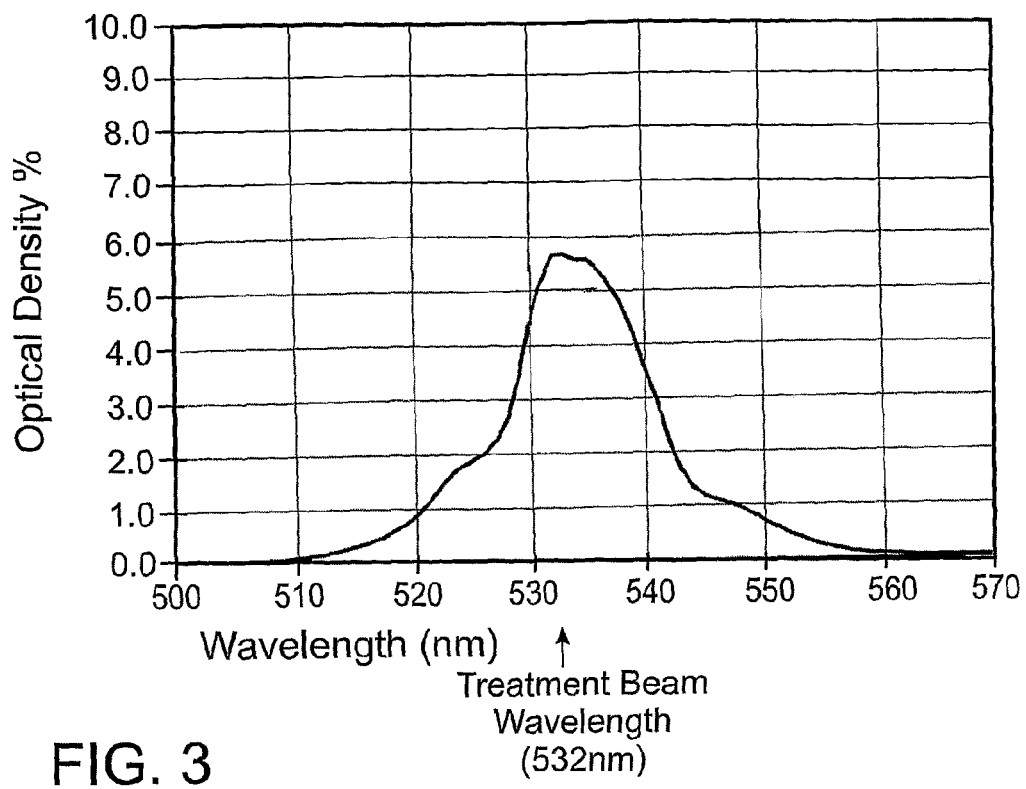
FIG. 3 is a graph showing the optical density achievable at the laser treatment beam wavelength for one embodiment of a dielectric coating.

FIG. 3 is a graph which demonstrates the optical density which is achievable at the treatment laser wavelength using the design of this invention. In this example an optical density over 5.5 is achieved at the treatment laser wavelength of 532 nm which is sufficient to avoid the need of additional safety filters to protect the viewer 14, in most cases. A multi-layer dielectric coating which can produce this optical density would distort the substrate in prior art designs resulting in astigmatism, however the thicker, wedge optic design of this invention avoids this problem.

Figure 4:
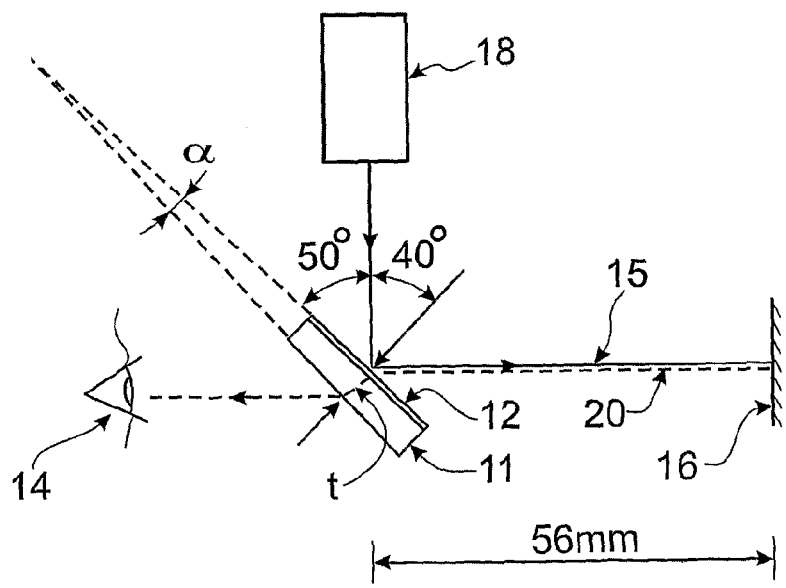
FIG. 4 is a block diagram showing details of a preferred embodiment showing the relationship of thickness at the central beam axis and wedge angle.

A preferred embodiment of this invention is shown in FIG. 4. In this example the wedge angle ($\alpha$) can be chosen for different thicknesses (t) at the central axis as follows:

| t | $\alpha$ (arcmin) |
|---|---|
| 2.0 mm | 13.0 |
| 2.5 mm | 16.5 |
| 3.0 mm | 21.0 |

These values, and the optimum wedge angle for other thickness values, can be calculated using computer based ray tracing software that provides astigmatism values. By modelling the required substrate thickness value the wedge angle is selected to give a minimum astigmatism value in the viewing path 15.

The substrate material can be chosen based on a comparison of the thermal expansion coefficients of the substrate and the structure and materials used for the hard dielectric coating. For example, hard dielectric coatings can be constructed from multiple alternate layers of silica and hafnia. The thermal expansion coefficients of silica and hafnia are $0.59 \times 10^{-6}$/° C. and $4.6 \times 10^{-6}$/° C. By choosing fused silica as the substrate material the residual stresses produced by the coating process can be minimised as compared to the use of BK7 glass which has a thermal expansion coefficient of $8.3 \, mm \times 10^{-6}$/° C.

The present invention provides a beam blocking and combining optic which can combine a laser beam into a viewing path with very low astigmatism in the viewing path and in the reflected laser beam, while also providing high optical density filtering of the laser wavelength to protect the viewer.

Throughout the specification the aim has been to describe the preferred embodiments of the invention without limiting the invention to any one embodiment or specific collection of features. Various modifications and variations will be evident to persons skilled in the art which fall within the broad scope of the invention.

The invention claimed is:

1. A beam blocking and combining optic comprising:
    a wedged optically transparent substrate with a hard dielectric coating applied to a beam combining side of the substrate, the hard dielectric coating having a high reflectance at a laser wavelength and controlled transmittance at visible wavelengths,
    wherein the substrate is designed with a wedge angle chosen to minimize astigmatism when viewing through the substrate and the hard dielectric coating is designed to maintain good colour balance in a viewing path between a viewer and a target while protecting the viewer from reflected laser radiation, wherein the beam blocking and combining optic combines a laser beam into the viewing path, the laser beam including a laser aiming beam and a laser treatment beam, and wherein the hard dielectric coating has an optical density of over 5.5 at the wavelength of the laser treatment beam.

2. The beam blocking and combining optic of claim 1, wherein the substrate material is selected so that the thermal expansion coefficient of the substrate matches that of the dielectric coating, in order to minimize stress and as a result minimize curvature of the substrate, resulting in further reduction of laser beam astigmatism.

3. The beam blocking and combining optic of claim 1, wherein the optically transparent substrate is made between 2mm and 5mm thick at the central beam axis in order to reduce the curvature of the substrate caused by residual stress induced by the application of the dielectric coating, thereby resulting in minimal laser beam astigmatism.

4. The beam blocking and combining optic of claim 1, wherein the substrate has an anti-reflection coating on an opposite side of the substrate to the hard dielectric coating.

5. The beam blocking and combining optic of claim 4, wherein the anti-reflection coating is designed to minimize reflection over the visible wavelength range.

6. The beam blocking and combining optic of claim 1, wherein the hard dielectric coating is constructed from multiple alternate layers of silicia and hafnia.

7. The beam blocking and combining optic of claim 1, wherein the substrate material is fused silica.

8. The beam blocking and combining optic of claim 1, wherein the substrate is designed with a wedge angle chosen for different thicknesses at the central beam axis.

9. The beam blocking and combining optic of claim 1, wherein the beam blocking and combining optic minimizes astigmatism in the viewing path and in the reflected laser beam.

10. The beam blocking and combining optic of claim 1, wherein the hard dielectric coating directs the laser beam into the viewing path and protects the viewer from the reflected laser radiation.

11. The beam blocking and combining optic of claim 1, wherein the hard dielectric coating partially reflects the laser aiming beam to the target and partially transmits the laser aiming beam to the viewer.

12. The beam blocking and combining optic of claim 1, wherein the hard dielectric coating reflects the laser treatment beam to the target and blocks scattered or reflected laser treatment radiation from the target to the viewer.

13. The beam blocking and combining optic of claim 1, wherein the hard dielectric coating is designed using multiple layers to form an interference filter with controlled transmission over the visible spectrum.

14. The beam blocking and combining optic of claim 13, wherein the interference filter controls transmission to visually compensate for the wavelength of the laser treatment beam which is reflectively blocked to minimize colour distortion in the viewing path.

15. The beam blocking and combining optic of claim 14, wherein colour distortion in the viewing path is minimized when a wavelength in the green spectral range is blocked by gradually reducing transmission of increasing wavelength in the red spectral range and decreasing wavelength in the blue spectral range.

16. The beam blocking and combining optic of claim 14, wherein colour distortion in the viewing path is minimized when a wavelength of 532 nm is blocked by gradually reducing transmission for wavelengths above 580 nm and below 460 nm.

* * * * *